United States Patent [19]

Castle

[11] 4,165,269
[45] Aug. 21, 1979

[54] METHOD OF MAKING HALOGENATED ACETYLENES

[75] Inventor: Peter M. Castle, Penn Hills, Pa.

[73] Assignee: Westinghouse Electric Corp., Pittsburgh, Pa.

[21] Appl. No.: 939,554

[22] Filed: Sep. 5, 1978

[51] Int. Cl.$^2$ .............................................. B01J 1/10
[52] U.S. Cl. ........................ 204/163 R; 204/DIG. 11
[58] Field of Search ... 204/158 HA, 163 R, DIG. 11; 260/654 D

[56] References Cited

U.S. PATENT DOCUMENTS

| | | | |
|---|---|---|---|
| 1,325,214 | 12/1919 | Snelling | 204/163 R |
| 2,674,573 | 4/1954 | Crauland | 204/163 R |

OTHER PUBLICATIONS

Shaub et al., International Journal of Chemical Kinetics (1975) VII, pp. 509–529.

Primary Examiner—Howard S. Williams
Attorney, Agent, or Firm—R. D. Fuerle

[57] ABSTRACT

Halogenated acetylenic compounds are prepared by irradiating a mixture of a reactant and a sensitizer with coherent light. The reactant has the general formula $R-C_2HX_4$, $R-C_2H_2X_3$, or $R-C_2HX_2$ where X is Cl, Br, or I, and R is H or another non-interfering group. The sensitizer has a higher thermal activation energy for its lowest energy dissociation reaction than does any part of said reactant.

10 Claims, 1 Drawing Figure

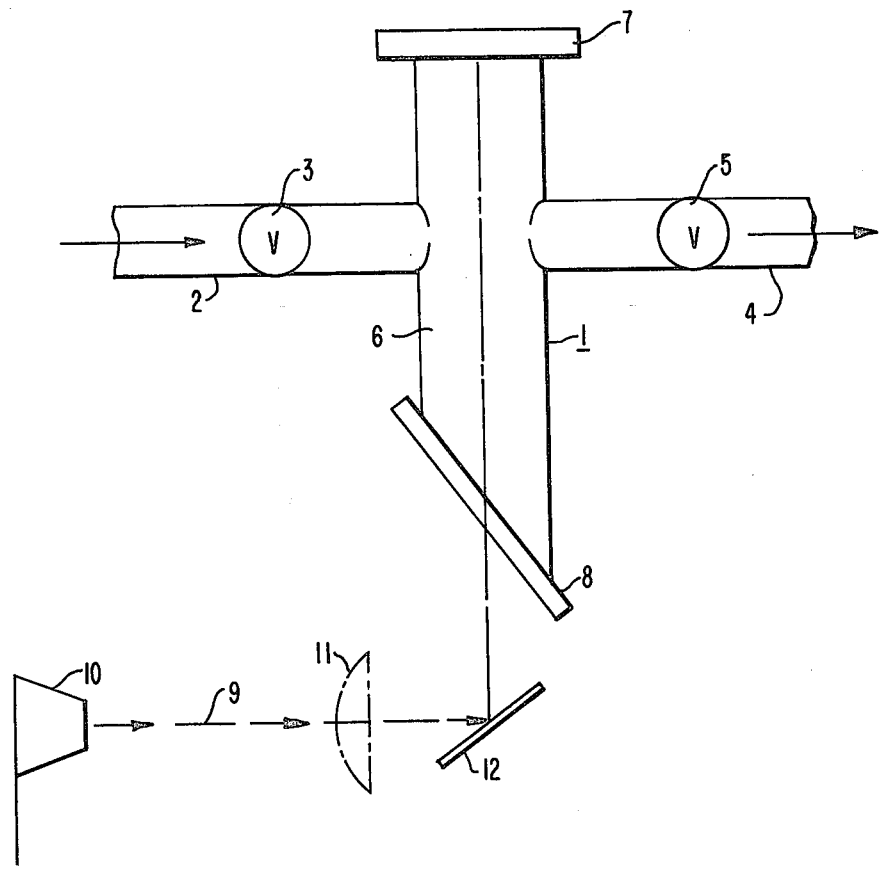

METHOD OF MAKING HALOGENATED ACETYLENES

BACKGROUND OF THE INVENTION

Laser-induced chemical reactions are the subject of an intense and rapidly growing research effort directed toward the production of novel chemical compounds, the development of energy efficient processing techniques, and isotope separation schemes. The direct approach in most of these studies is to attempt to excite a specific bond in a molecule with a laser photon in such a way that a specific bond is broken and another formed at the same place. The laser is applied as a molecular knife and welding tool in order to cut apart specific parts of molecules and weld them to others to bring about unique chemical reactions.

In such a well defined system of photons and absorbers, any collisional transfer of absorbed energy would be a loss in efficiency as well as a source of indiscriminate energy to be supplied to uncontrolled side reactions. Most laser chemistry experiments are designed in such a way as to keep the collisional energy transfer to a minimum. The technique of LPHP (Laser Powered Homogeneous Pyrolysis), developed by Shaub and Bauer, takes advantage of this energy transfer process of effect molecular decompositions. The absorption of energy from a focused or unfocused laser beam by a molecule of high stability can create very high local temperatures in the vicinity of the beam. The temperature, which is a function of the laser power and the absorption cross section, can easily be in excess of 1000° C. If there are reasonable numbers of collisions of laser excited sensitizer molecules with reactant molecules which are less stable to thermal degradation or reaction and, in addition, which accept energy in an efficient transfer process from the laser excited molecules, there can be a rapid thermal reaction of the reactant molecules. The success of the energy transfer process depends on the stability of the sensitizer molecule. Thus, there are three criteria which must be satisfied by the sensitizer molecule: high absorbing cross section at a laser wavelength (the process need not be restricted to the utilization of $CO_2$ lasers), high thermal stability in the sensitizer absorbing molecule, and a moderately fast collisional relaxation time.

PRIOR ART

An article by W. M. Shaub and S. H. Bauer in the International Journal of Chemical Kinetics 1975, VII, pages 509 to 529 showed the irradiation by laser of a mixture of $CF_2Cl_2$ and ethane to produce acetylene in low yields. The article also showed the elimination of HCl from tert-butyl chloride to produce isobutylene.

SUMMARY OF THE INVENTION

I have discovered that hydrogen halides can be eliminated from dihalo ethylenes or from tri or tetra halo ethanes to produce halogenated acetylenes. Although the chloroacetylenes are unstable and even explosive, I have been able to produce them in quantitative yields. The halogenated acetylenes of this invention are very useful in chemical research and in the production of other chemicals.

DESCRIPTION OF THE INVENTION

The accompanying drawing is a diagrammatic side view of a certain presently preferred embodiment of an apparatus used in the practice of this invention.

In the drawing, reaction vessel 1 comprises a reaction mixture inlet 2 controlled by valve 3 and a product and reactant recovery outlet 4 controlled by valve 5. In the center of reaction vessel 1 is a reaction chamber 6 having a mirror 7 at one end and a Brewster angle window 8 at the other. The reaction mixture is admitted through reaction mixture inlet 2 into reaction chamber 6. Coherent monochromatic light 9 from laser 10 passes through optional focusing element 11 and is reflected off mirror 12 through Brewster angle window 8 into reaction chamber 6 causing the reaction to occur. The products and unreacted reaction mixture are recovered through outlet 4. Batch or continuous processing may be used.

THE REACTANT

The reactant is a compound having the general formula $R-C_2H_2X_3$ or $R-C_2HX_2$ where each X is independently selected from Cl, Br, and I and R is H or a group which does not undergo a thermal process at an activation energy which is lower than the activation energy for HX elimination from the reactant. These general formulae encompass dihalo ethylenes having the general formulae $R-CH=CX_2$ and $R-CX=CHX$, trihalo ethane having the general formulae $R-CX_2-CH_2X$, $R-CH_2-CX_3$, and $R-CHX-CHX_2$, and tetrahalo ethanes having the general formulae $R-CX_2-CHX_2$ and $R-CHX-CX_3$. The $R-CX=CHX$ and the tetahalo alkanes may produce allenes instead of acetylenes. In the formula, R may be aliphatic, aromatic, or hetero, and X is preferably chloro as the chloro compounds have been tried and work well. A preferred reactant is 1,1,1-trichloroethane as it has been found to work very well.

THE SENSITIZER

The sensitizer is a compound which absorbs the laser energy and transfers it as heat to the reactant. In performing this function it acts as a catalyst and is not used up. The sensitizer therefore must have a higher thermal activation energy for its lowest energy dissociation reaction than any part of the reactant.

It is also important that the sensitizer have a moderately fast collisional relaxation time of less than 500 microseconds so that energy is not lost by interaction with the walls of the reactor.

An absorbing cross-section at the laser wavelength sufficient for complete absorption at 20 to 50 Torr and 10 cm. path length is also important.

Examples of sensitizers include $CF_2Cl_2$, $CF_3Cl$, $CFCl_3$, and $SiF_4$. The preferred sensitizer is $CF_2Cl_2$ because it has been tried and has been found to work very well. The $CF_2Cl_2$ sensitizer absorbs at 927 and 1079.7 cm.$^{-1}$. Both the sensitizer and the reactant are preferably gases as it is difficult to pump energy into a liquid.

The sensitizer may be mixed with the reactant in any proportion, but it is preferable to use more reactant than sensitizer. In fact, the amount of reactant may exceed the amount of sensitizer by five times or more. If the sensitizer in the mixture is $CF_2Cl_2$, it is preferably under a pressure of at least 20 Torr for laser powers under 10 watts per $cm^2$ because it seems to be a threshold for the proper temperature profile.

THE LASER

The laser power needed will depend upon the sensitizer pressure and cross-section. Infrared laser wavelengths are preferred because at infrared wavelengths vibrational excitation is more quickly and efficiently transferred to a Boltzmann distribution thermal energy. A preferred laser is the $CO_2$ laser at 920 to 1100 $cm^{-1}$. The CO, HF, DF, $N_2O$, OCS laser and hybrids such as Nd-YAG with parametric oscillators can also be used. In any case, the light must be coherent.

THE METHOD

The laser beam is directed incident on a cell containing the mixture of the reactant and the sensitizer. The reaction seems to proceed in a series of steps, here illustrated with Freon 12 ($CF_2Cl_2$) and 1,1,1-trichloroethane:

$$CF_2Cl_2 + h\nu \rightarrow CF_2Cl_2^*$$

$$CF_2Cl_2^* + Cl_3C-CH_3 \rightarrow Cl_3C-CH_3^* + CF_2Cl_2$$

$$Cl_3C-CH_3^* \rightarrow Cl_2C=CH_2 + HCl$$

$$CF_2Cl_2^* + Cl_2C=CH_2 \rightarrow Cl_2C=CH_2^* + CF_2Cl_2$$

$$Cl_2C=CH_2^* \rightarrow ClC\equiv CH + HCl$$

The reactions are usually performed at room temperature although it may be desirable to cool some reactions.

The products formed may be easily removed if they are solids or liquids and the reactant and sensitizer are gases. If the products are gases, they can be removed by techniques known in the art such as cold trapping and selective adsorption.

The following example further illustrates this invention.

EXAMPLE

This example involves the chemical reaction:

$$CCl_2=CHCl + CF_2Cl_2^* \rightarrow ClC\equiv CCl + HCl + CF_2Cl_2$$

Trichloroethylene     Dichloroacetylene

In carrying out the example reaction the following conditions were used:
Trichloroethylene—60 torr
Dichlorodifluoromethane—20 torr
Laser wavelength—9.2605 micrometers
Laser power—6.2 watts (focused with a 1"f/1.0 lens) CW
Irradiation time—120 seconds After an irradiation time under the above-listed conditions, approximately 10 torr of the product dichloroacetylene were produced. These values pertain to a reaction vessel volume of about 75 cc. Thus, approximately 40 micromoles were produced in 120 seconds.

In order to improve the efficiency of the reaction it is necessary to irradiate in a vertical direction. This minimizes the contamination of the cell windows. In addition, such vacuum sealing agents such as Apiezon grease, black wax, RTV (silicon rubber) as are commonly used in the vacuum practice cannot be utilized because these formulations react readily with dihaloacetylenes. The reaction vessels employed in this example were constructed using KCl irradiation windows sealed with epoxy cement to pyrex bodies whose stopcocks were treated with silicone grease.

The reaction has also been carried out under pulsed laser irradiation at the same wavelength. The results were similar when unfocused radiation, having a pulse duration of 100 nanoseconds ($\pm 50$) and an energy density of at least 0.5 joules/$cm^2$/pulse, was directed into a cell in which the other experimental parameters were similar. The yields appear to be higher in this example. This may be due to the less generalized heating of the reaction mixture.

I claim:
1. A method of making halogenated acetylenic compounds comprising:
    (A) forming a mixture of
        (1) a reactant selected from the group consisting of compounds having the general formula $R-C_2H_2X_3$ and $R-C_2HX_2$, where each X is independently selected from Cl, Br, and I, and R is H or a group which does not undergo a thermal process at an activation energy which is lower than the activation energy for HX elimination from said reactant;
        (2) a sensitizer which:
            (a) has a higher thermal activation energy for its lowest energy dissociation reaction than does any part of said reactant,
            (b) has a collisonal relaxation time less than 500 microseconds,
            (c) has an absorbing cross section at the wavelength such that complete absorption occurs at about 20 to about 50 torr and 10 cm path length;
    (B) irradiating said mixture with coherent light at said wavelength.
2. A method according to claim 1 wherein said reactant and said sensitizer are gases.
3. A method according to claim 1 wherein said reactant is a dichloroethane.
4. A method according to claim 1 wherein said reactant is 1,1,1-trichloroethane.
5. A method according to claim 1 wherein said sensitizer is selected from the group consisting of $CF_2Cl_2$, $CF_3Cl$, $CFCl_3$, and $SiF_4$.
6. A method according to claim 5 wherein said sensitizer is $CF_2Cl_2$.
7. A method according to claim 1 wherein said reactant does not absorb at said wavelength.
8. A method according to claim 1 wherein the amount of reactant in said mixture is at least 5 times the amount of sensitizer.
9. A method according to claim 1 wherein said wavelength is in the infrared.
10. A method according to claim 9 wherein said wavelength is about 920 to about 1100 $cm^{-1}$.

* * * * *